United States Patent [19]

LeVeen

[11] 3,991,770

[45] Nov. 16, 1976

[54] METHOD FOR TREATING BENIGN AND MALIGNANT TUMORS UTILIZING RADIO FREQUENCY, ELECTROMAGNETIC RADIATION

[76] Inventor: Harry H. LeVeen, 800 Poly Place, Brooklyn, N.Y. 11209

[22] Filed: Dec. 23, 1975

[21] Appl. No.: 643,661

Related U.S. Application Data

[63] Continuation-in-part of Ser. No. 595,094, July 11, 1975, abandoned, which is a continuation-in-part of Ser. No. 436,102, Jan. 24, 1974, abandoned.

[52] U.S. Cl. .............................. 128/413; 128/404; 128/422
[51] Int. Cl.² ........................................ A61N 1/40
[58] Field of Search........ 128/413, 404, 405, 419 R, 128/422, 399, 1.3–1.5

[56] References Cited
UNITED STATES PATENTS

| | | | |
|---|---|---|---|
| 2,223,447 | 12/1940 | Hathaway | 128/413 |
| 2,407,690 | 9/1946 | Southworth | 128/422 |
| 3,181,535 | 5/1965 | Milinowski | 128/422 |
| 3,245,408 | 4/1966 | Gonser | 128/422 |

FOREIGN PATENTS OR APPLICATIONS

| | | | |
|---|---|---|---|
| 1,284,528 | 12/1968 | Germany | 128/1.5 |
| 618,179 | 2/1949 | United Kingdom | 128/413 |
| 353,231 | 7/1931 | United Kingdom | 128/413 |

OTHER PUBLICATIONS

Geyser, "Diathermic . . . Cancer," Jan., 1925, Fisher's Magazine.

Warren, "Preliminary Study . . . Tumor Cases," The Am. J. of Roentgen & Radium Therapy, vol. 33, No. 1, Jan. 1935, pp. 75–87.

LeVeen, "Physiological . . . Burn Therapy," Chic. Med. School Quarterly, vol. 17, No. 2, Feb. 1956, pp. 49–58.

Muckle, et al., "The Sel. Inhibitory . . . Malignant Cells," Brit. J. Cancer, vol. 25, No. 4, pp. 771–778, 1971.

Goldenberg, et al., "Direct & Abscopal . . . Hyperthermia," Zeitschrift fur Natur For., 8, 26:1971, pp. 359–361.

*Primary Examiner*—Robert W. Michell
*Assistant Examiner*—Lee S. Cohen
*Attorney, Agent, or Firm*—Brooks Haidt Haffner & Delahunty

[57] ABSTRACT

A method of treating tumors, both benign and malignant, such as carcinoma, sarcoma, cysts and avascular lesions, in animals, such as humans, by radio frequency heating at the location of the tumor in the host with intensity and duration sufficient to cause necrosis of the tumor tissue. Substantial damage to the surrounding normal tissue is avoided, as the surrounding normal tissue is cooled by blood flow which carries the heat away to dissipate such heat in those portions of the body not being subjected to heating.

4 Claims, 6 Drawing Figures

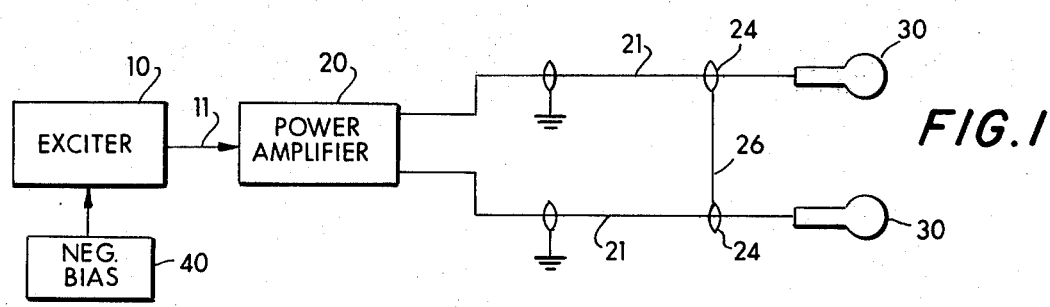
FIG. 1
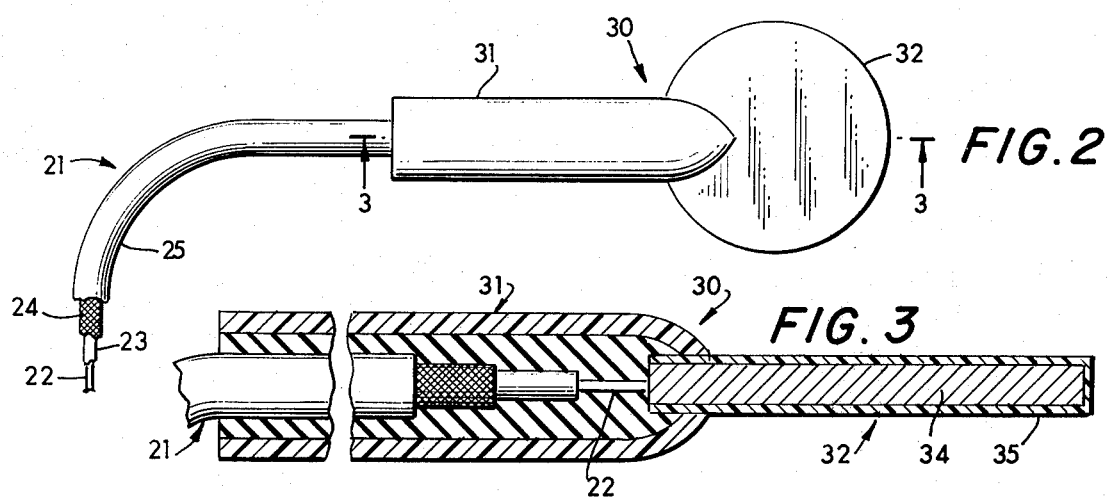
FIG. 2
FIG. 3
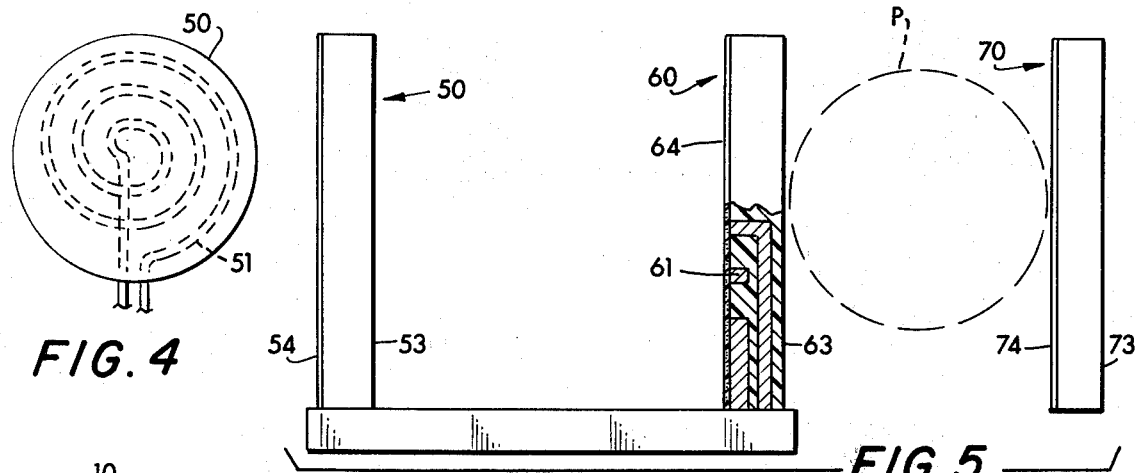
FIG. 4
FIG. 5
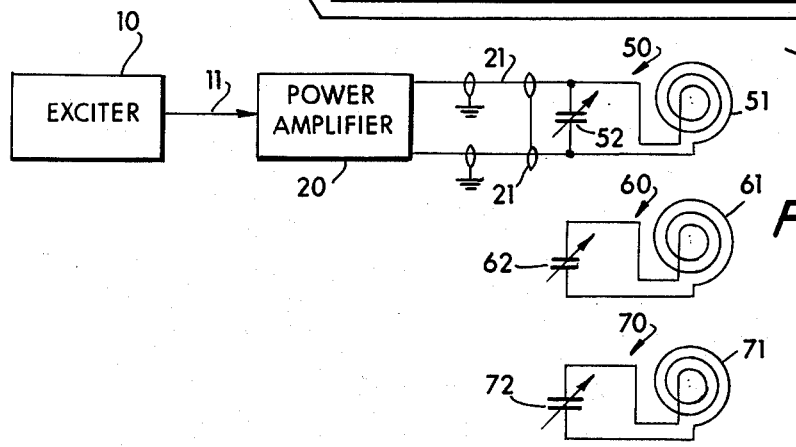
FIG. 6

METHOD FOR TREATING BENIGN AND MALIGNANT TUMORS UTILIZING RADIO FREQUENCY, ELECTROMAGNETIC RADIATION

RELATED CASES

This application is a continuation-in-part of LeVeen application Ser. No. 595,094, filed July 11, 1975 now abandoned, which is in turn a continuation-in-part of LeVeen application Ser. No. 436,102, filed Jan. 24, 1974 (now abandoned), and is related to LeVeen application Ser. No. 595,095, field July 11, 1975 (now abandoned).

This invention relates to the treatment of tumors in animal hosts, such as human beings, and in particular provides a technique for destroying the tumor without injury to adjacent normal tissues. The tumors can be either benign or malignant and include carcinomas, sarcomas, cysts and avascular lesions.

It is an important object of this invention to provide a method applicable to the treatment of tumors under a wide variety of conditions which can be utilized with a minimum, and preferably an absence, of surgery.

It has been noted that tumors can be affected by hyperthermia (Brit. of Cancer 25:771, 1971; Cancer Research 32:1916, 1972). This observation was coupled with the statement that the tumors were heat sensitive. Experiments with external surface heating do not produce deep heating and in some cases, using hyperthermia, the whole animal was heated as much as the tumor. Others have felt that a slight raise in temperatures produced by metabolic changes in the cancer interfered with cell growth (Europ. J. Cancer 9:103, 1973). Others have heated tumors for a few degrees by diathermy to observe the effect on the tumor which was inhibitory but not obstructive (Zeit. fur Naturforschung 8, 26:359, 1971). There is still considerable disagreement and conflicting evidence of the role heat may play in the treatment of cancer (The Lancet, May 3, 1975; 1027).

Anatomical studies suggest that the blood flow through carcinomas and other neoplasms is sluggish (Acta Pathalogica Microbiologica Scand., 22:625, 1945; Advances in Biology of the Skin, 21:123, 1961). Tumors possess an angiogenetic factor which initiates the formation of new blood vessels. These blood vessels, however, are capillaries which because of their small diameter offer great resistance to blood flow. The capillaries make connections with the normal capillaries on the periphery of the tumor and are tortuous following haphazard pathways before emptying into some small vein at the periphery of the tumor. Frequentlyl there is marked venous obstruction within the tumor caused by compression of the peripheral veins due to enlargement of the tumor and sometimes due to ingrowth of tumor cells into the blood vessels obstructing them.

Anatomical studies also demonstrate the presence of arterio-venous fistulae at the periphery of tumors which can cause the tumors to appear vascular and angiography because of the rapid appearance of contrast media, but which actually deprive the tumor of the blood supply. The arterio-venous fistulae at the periphery of the tumor tend to create a low resistance pathway at the surface of the tumor which lowers the arterial pressure and diverts blood from entering the tumor.

Although anatomical studies suggest that the tumor blood flow is diminished and slow, only angiographic studies have functionally confirmed that blood flow through tumors is actually sluggish giving rise to an appearance of non-filling on angiography. Residual contrast medium remains in the tumor after it has been swept out of the adjacent normal tissue by normal blood flow. This remaining residual contrast medium has been called a "Tumor Stain." The tumors which have been studied radiographically have been brain tumors and kidney tumors.

This has been confirmed by the applicant by the indicator dilution technique measuring the actual flow of blood through normal tissue and through tumors. The indicator dilution technique is more reliable than the visual method as seen on angiography. Such studies were done in vivo using X-ray contrast medium dilution and in vitro on excised specimens. In the excised specimens blood flow was measured by indicator dilution technique using radioiodinated serum albumin. The albumin molecule was tagged with $I_{131}$ and the isotope dilution was measured in the tumor and in normal tissue by a columnated scintillation counter. These studies indicated that the magnitude of flow through the adjacent normal tissue is such that the tumor tissue is differentially heated when the area of the body containing the tumor is treated by diathermy.

In accordance with this invention, tumors are destroyed in humans and other animals by heating the portion of the body containing the tumor such that the temperature of the tumor is raised to a point at which the tumor is necrosed, i.e., at or above about 50° C. In some instances necrosis of the tumor is achieved at temperatures as low as 46° C. Such temperatures, of course, also destroy or severely damage normal tissue and the present invention is based on the discovery that when a portion of the body is heated, for example, by applied radio frequency electromagnetic radiation, the tumor is heated differentially to a greater extent, such that the temperature of the normal tissue adjacent the tumor can be kept below 40° C.

This is caused primarily by the normal blood flow in the adjacent normal non-cancerous tissue. Thus, the temperature at which tissue is heated depends upon the blood supply to the tissue. Although the blood itself is heated, it serves to carry heat away from the part being heated. As a result, tissues which are poorly perfused with blood become heated more rapidly and to a higher temperature than tissues which have a normal rate of blood flow. As pointed out above, cancerous and other malignant and benign growths develop outside a preformed blood vessel distribution network and derive their blood supply from the periphery of the tumor where it meets the adjacent normal blood supply. As a consequence, the slow rate and volume of blood flow through the tumor provides a lesser cooling rate in the tumor than the flow of blood through the normal tissues adjacent the tumor.

Thus, when, for example, diathermy is applied in vivo to tissue containing a tumor, the tumor is heated more than the adjacent normal tissue. If the applied radiation is of sufficient intensity and for a sufficient duration of time the differential heating of the tumor can necrose the tumor without significant thermal injury to the adjacent normal tissue.

In accordance with this invention diathermy can be used to produce differential heating of cancerous tissue in the body. Insulated applicators, which are connected to the output of an R.F. generator, are placed on opposite sides of the portion of the body adjacent the location of the tumor such that the applicators produce localized heating in the tumor differentially higher than the remaining normal tissue, adjacent to the tumor, which is in the path of the R.F. radiation, i.e., generally between the applicators. Heating the tissue between the applicators is continued for a duration of time and at an intensity sufficient to cause necrosis of the tumor by heating the tumor to about 50° C or above. In some cases tumor necrosis can be caused by heating to temperatures as low as 46° C. In any event heating is insufficient to raise the temperature of the surrounding normal tissue to cause significant damage to that tissue because such adjacent tissue is cooled by its normal blood supply.

This effect of destroying tumors by differential heating has been confirmed in both human cancers and cancers in animals by simultaneous measurement of the temperature in the tumor and in the adjacent normal tissue. Differential thermometry between the tumor and normal tissue is performed with non-metallic thermometers having non-electrolyte fluids, such as liquid alcohol filled thermometers. Normal tissue is irreversibly damaged at temperatures above 50° C. (Chic. Med. Sch. Q 17:49, 1956). Temperatures as high as 60° C can easily be achieved in the tumor while the adjacent normal tissue is heated only to the vicinity of 40° C using about 100 watts of energy at 13.56 MHz.

Generally, the radio frequencies employed should be as low as permissible in order to enhance the absorption of the energy by the tissue. Consequently, the lower frequencies permitted by the F.C.C. are preferable. Since most tumors are located within the body, penetration of the heating radiation through the location of the tumor is essential. It is well known that penetration of the body by electromagnetic radiation and absorption of the energy of that radiation is an inverse function of frequency. Generally, the practical frequency range for use of diathermy as described above to produce internal heating which can be utilized in the treatment of tumors in accordance with this invention is from about 100 kiloHertz to about 200 megaHertz. As in this range the longer wavelengths are both more effective in terms of heating and less likely to cause damage by scattering and the like, as occurs in the microwave region, the preference is distinctly for the longer wavelengths. The preferred frequency for treatment is 13.56 megaHertz because it is the longest wavelength presently permitted by law.

With impedance matching the results of this invention are generally achieved with energies ranging between 50 and 250 watts and for periods of times typically of 10 to 20 minutes, although lower and higher power levels and longer and shorter periods of time can be used depending on the size and location of the tumor. The conventional diathermy machine can not provide the necessary heat and has the disadvantage that the distribution of heat in the tissues is apt to be non-uniform and can not always be predicted. Also a considerable amount of energy on the standard diathermy machine is often reflected back into the diathermy machine without entering the tissue. Thus, it is difficult to determine the dosage. Utilizing the energies required in accordance with this invention, the conventional machine itself and the cables become very overheated. These problems are readily overcome utilizing higher power output R.F. generators and heavier cables so that energies on the order required can be applied to the portion of the body under treatment. Generally, the construction of suitable R.F. generators and transmission cables are not unlike those utilized in industry for relatively low power outputs, i.e., on the order of 1 kilowatt in the frequency range under consideration. While such a power level is high for diathermy use, it is not uncommon in many other applications, including radiotelephony, induction heating, and the like. The basic equipment is thus conventional.

It is preferred in present usage to employ an applicator generally having the shape of a paddle, i.e., having a handle and a round plate more or less coplanar with the end of the handle. The plate itself is a conductive metal disc which is coated with an insulating film of non-glossy material, such as a coating of polyurethane resin, and is connected to the power source through the handle of the applicator. Suitable applicators which have been used have copper plates 2 inches to 4 inches in diameter. Also flat copper spirals have been used with success. The leads to the applicators from the power amplifier, of course, are necessarily insulated and preferably are shielded cables, such as coaxial cables, with the outer shield grounded, as peak voltages on the order of 300 volts are developed in the output circuit of the R.F. amplifier. The applicators and cables should be waterproof and be sterilized before use.

The applicators are connected across the radio frequency output in the present usage of an amplifier capable of up to 2000 watt output. The impedance of the load, i.e., the body portion between the applicators, is of course variable, thus, the normal impedance matching procedures utilized in coupling the output circuits of an R.F. generator through a transmission line to a load can be utilized. The transmission line, i.e., coaxial cables, are connected appropriately at the output tank coil or otherwise in the final stage of the R.F. generator to provide a proper impedance match to the transmission line and impedance matching of the end of the transmission line, i.e., the applicators, to the load is important. In some circumstances, it has been found feasible to use fixed impedance matching at the applicators by building series inductance in the handles of the applicators, but this is not necessary as separate adjustable provision for matching the load can be utilized. Without proper impedance matching the power requirements are much greater and damage to the R.F. amplifier can occur.

Although it is not essential in carrying out the process of this invention, desirably in a sophisticated unit, provision is thus made for measuring both forward and reflected power. Similarly, fail-safe precautions should be utilized to prevent a control failure resulting in application of full load of the R.F. generator to the applicators when only a partial load is desired.

Selective heating of tumors in accordance with the present invention utilizing radio frequency electromagnetic energy can be further accentuated by the use of drugs. Vasodilators increase tissue blood flow, but reduce the blood flow to tumors and further decrease the tumor oxygen tension (Acta Radiol 58:401–434, 1962; Cancer 20:60–65, 1967). The use of vasodilators in connection with radio frequency treatment in accordance with the present invention should be of beneficial effect both because of the increased flow produced through contiguous normal tissue will better dissipate heat generated by the radio frequency energy while the slower flow through the tumor will accentuate the elevation of the tumor temperature.

It has also been noted that with hypotension, perfusion of blood through a tumor ceases and the tumor blanches (J. Natl. Canc. Instit. 12:399–410, 1951). Consequently, the use of hypotensive agents can improve the effects of radio frequency treatment in accordance with the present invention. Similarly, radiation, tumor embolism, alteration of blood viscosity and compression can all be used to advantage.

When the tumor tissue has been necrosed it becomes a fluid. This fluid may be removed naturally by the body but aspiration has also been found desirable at times. Care should be taken to prevent sepsis and the use of antibiotics may be indicated.

Treatment in accordance with the present invention should be with care to avoid overheating normal tissues such as cartilage which have no blood supply. The presence of bile in the gall bladder may also cause a problem when treatment requires application to a portion of the body including the gall bladder.

For a more complete understanding of the practical application of this invention, reference is made to the appended drawings in which:

FIG. 1 is a block diagram indicating an apparatus set-up for carrying out the process of this invention;

FIG. 2 is a plan view of an applicator suitable for carrying out the process of this invention;

FIG. 3 is an enlarged, fragmentary section taken at line 3–3 in FIG. 2;

FIG. 4 is an end view of a portion of another applicator suitable for carrying out the process of this invention;

FIG. 5 is an elevational view of the applicator shown in FIG. 4 indicating its use in relation to the portion of the body being treated; and FIG. 6 is an electrical schematic diagram of the applicator shown in FIGS. 4 and 5.

Referring to FIG. 1, a simple arrangement of apparatus for carrying out the process of this invention involves an exciter 10, a power amplifier 20, and a pair of applicators 30. Both the exciter 10 and power amplifier 20 are conventional. Exciter 10 has a crystal controlled oscillator, in the illustrated case operating on 13.56 mHz. Exciter 10 has an output of between 2 watts and 110 watts dependent on the bias of the oscillator; the less negative the bias the higher the output of exciter 10. An oscillator variable bias supply 40 functions to control the bias and the oscillator and hence the output of exciter 10.

Power amplifier 20 is designed to amplify the output of exciter 10, and to this end the output circuit of exciter 10 is connected to the input circuit of power amplifier 20 as denoted by the reference numeral 11. Power amplifier 20 is designed for an output of 30 watts to 1,000 watts dependent upon the output of exciter 10, and, of course, is tuned to the same frequency of 13.56 mHz.

The output circuit of power amplifier 20 is connected to energize applicators 30 by means of coaxial cables 21. Cables 21 have their inner conductors 22 connected across the tank circuit of the output of power amplifier 20 and lead to applicators 30, as more fully described with respect to FIGS. 2 and 3. As shown in FIG. 2, each coaxial cable 21 includes a central conductor 22 which is provided with insulation 23 over which there is a braided shield 24 and an outer jacket 25. The two conductors 22 are connected across the tank coil in the output circuit of power amplifier 20, or optionally one can be grounded. In either case, the two shields 24 are grounded at the power amplifier, and, as shown in FIG. 1, are preferably also provided with an interconnection 26 between shields 24 adjacent the handle 31 of each applicator 30.

Generally applicators 30, as can be seen best in FIG. 2, are in the shape of a paddle having a handle 31 and an applicator portion 32. Each handle 31 is made of insulating material, such as a phenolic resin, and, as can be seen best in FIG. 3, is hollow such that coaxial cable 21 is brought into the end of handle 31. The applicator portion 32 is secured to handle 31 at the end of handle 31 opposite that into which cable 21 leads and is in the form of a flat, circular copper disc 34 which is electrically connected at its periphery adjacent the end of handle 31 to the end of conductor 22.

As illustrated in FIG. 3, copper plate 34 is provided with an insulating coating 35 such that electrical contact with plate 34 can only be made through conductor 22. Coating 35 should be of non-lossy insulating material in order to minimize the generation of heat in the insulation itself. Suitable insulation materials are characterized by low dissipation factors generally below about 0.01, and can be, for example, Mycalex (a proprietary glass and mica insulating material), polyethylene, polytetrafluoroethylene, polystyrene, and polyurethanes. Polyurethanes are particularly desirable since they are readily applied as liquids which set to form smooth, even and thin coatings.

Applicators 30 should have diameters such that when the portion of the body containing the tumor is placed between them they will be sufficiently large to place the entire tumor within the densest portion of the electromagnetic field set up when they are energized. It will be apparent that, as described above, applicators 30 function electrically as a capacitor such that the portion of the body between the electrodes is effectively between the plates of a capacitor. Heating occurs even though the body tissue is basically an electroyte rather than a dielectric material. The electric and magnetic fields which are set up, however, are those which would be set up between condenser plates.

It has also been found that heating in accordance with this invention can be obtained where the applicator structure is basically an inductance. Thus, referring to FIGS. 4, 5, and 6, there is shown an apparatus for developing and directing a radio frequency electromagnetic field in one direction with the energy confined to a desired region for localized heating of, for example, body tissue. The basic apparatus involves three essentially identical circuit units 50, 60, and 70.

Each unit 50, 60, and 70 includes a pancake coil 51, 61, and 71, respectively, which is in the form of a planar spiral of flat silver-plated copper having three turns from the inner to the outer end. Variable (0–250 pf) vacuum capacitors 52, 62, and 72 are respectively connected across each spiral coil 51, 61, and 71. Each spiral coil 51, 61, and 71 is housed in a circular polytetrafluoroethylene (PTFE) disc 53, 63, and 73, respectively, which is grooved appropriately to receive its associated spiral coil 51, 61, and 71 with the connections of such spiral coil extending from the PTFE disc for connection to its associated vacuum capacitor 52, 62, or 72. The open side of each PTFE disc, i.e., the side in which grooves are machined to receive the associated spiral, is covered with a thin plate of Mycalex 54, 64, and 74 to retain the associated spiral coil 51, 61, and 71, respectively, within its associated PTFE housing.

Unit 50 has its spiral coil 51 and capacitor 52 connected in parallel across the output of an R.F. power amplifier, such as amplifier 20, and is considered as the driver section which sets up an electromagnetic field when energized by power amplifier 20.

Unit 60 is mounted on a common housing of dielectric material with unit 50 such that they are parallel to each other and axially aligned spaced apart 6 inches when using a frequency of 13.56 mHz to energize unit 50. As a result, the electromagnetic field developed by unit 50 when energized is actually directed with regard to its magnetic component axially toward and through unit 60 (to the right as shown in FIG. 5). For convenience sake, unit 60 may be regarded as a focus section.

Unit 70 is positioned parallel to unit 60 and axially aligned with it on the side of unit 60 opposite unit 50 and functions as a reflector section confining the electromagnetic field such that an object placed between units 60 and 70 can be heated by the electromagnetic radiation between units 60 an 70. These units are then utilized in accordance with this invention in the same manner as applicators 30. At a frequency of 13.56 mHz, spiral coils 51, 61, and 71, each, can have three turns with an overall diameter on the largest turn of 5.5 inches and with the turns spaced about ⅜ inch on center. The distance between units 60 and 70 can be from 5 to 15 inches to accommodate the portion P of the doby to be treated.

In utilizing the arrangement of FIGS. 4, 5, and 6, the driver unit is adjusted by adjusting capacitor 52 into resonance with spiral 51. The impedance of the unit as described above should be about 50 ohms at this point. Units 60 and 70 are also adjusted by means of their associated condensers 62 and 72 to resonance, and maximum loading.

The above adjustments can all be made at a relatively low power output. The body portion P to be treated is then positioned between units 60 and 70 and the desired power output of amplifier 20 is then turned on to treat body portion P. In the following discussion, where the word "applicators" is used, reference is intended to applicators, such as applicators 30, and equally to applicators, such as units 60 and 70, unless the context clearly indicates otherwise.

Preferably, the applicators are placed firmly and in intimate contact with the surface of the body portion under treatment in order to minimize "hot spotting" which can occur when the surface of the body is of irregular contour. Indeed, such hot spotting is further minimized by using electrode paste on the surface of the portion of the body under treatment, and bronze wool or woven stainless steel in the form of a sleeve can be placed over the applicator further to minimize the effects of skin resistance. Such a sleeve typically is on the order of one-half to one inch thick, is compressible, and hence, takes up any irregularity on the surface contour of the body. Intimate contact, however, is not essential and in using fixed-tuned applicators it has been found that on occasion more effective results have been obtained by backing one of the applicators away from the surface of the body where the portion under treatment was relatively narrow and not optimum for the particular applicator.

Tissue temperatures during therapy can be determined by inserting into the tissue being heated non-metallic thermometers having non-electrolyte indicator fluids, such as glass alcohol thermometers. It is essential that during therapy the adjacent normal tissue temperature be raised only to 40° C, as higher temperatures can cause its destruction as well. With increased skill, a surgeon can avoid the necessity of using thermometers, as he can sense the temperature of the normal tissue by palpation when the diathermy is turned off. In order to destroy the tumor it is usually essential that its temperature be raised above 50° C. In some instances the tumor tissue can be necrosed at temperatures as low as 46° C. Destruction of the tumor can be observed either by thermometric means, by X-ray techniques used to sense the presence of the tumor, biopsy and the like.

In some intances, for example, cancer in some human organs, such as the liver, is treated by surgically exposing the organ to place the applicators directly in contact with the organ at the location of the cancer.

In the case of human lung carcinoma, both metastatic and primary, the applicators can be applied to the external chest wall. Massive necrosis of the lung tumor can induce complications of pulmonary abscess or hemorrhage, but these can be dealt with surgically after all the tumor has been destroyed.

Similarly, it may be necessary to divert the fecal stream with a proximal defunctionalizing colostomy, when rectal and colon tumors are treated to avoid the danger of necrosis with perforation.

Other avascular lesions occurring in otherwise normal tissue will respond equally to this therapy. Similarly, polycystic kidneys can be treated, since the cysts have no blood supply they will be heated while the vascular kidney substance will remain cool. Thus, the therapy will destroy the lining of the cyst wall which secretes fluid and causes compression atrophy of the normal kidney.

EXAMPLE I

A 67 year old white male had an unresectable carcinoma of the left lung which proved on biopsy to be a squamous cell. He had mild dyspenea and dull pain on the left side of his chest and a brachial neuralgia.

The apparatus generally described with reference to FIG. 1 was utilized, and applicators 30 were in the form of a pair of copper plates 34 of four inch diameter and one-eighth inch thickness. The applicators were fixed-tuned by incorporating in series between the connection of conductor 22 and plate 34 a coil located within handle 31 which consisted of six turns of 20 AWG copper wire with a one-half inch outside diameter (wound about a pencil) and one-half inch in length. The coil and its connections to conductor 22 and plate 34 were potted using silicone rubber composition within handle 31. Coaxial cable 21 was of the type known as RG 58-U and was three feet in length in each case. Insulated coating 35 was 4 mils thick and was a clear polyurethane resin containing no oxides.

The applicators 30 were positioned one flat against the anterior and the other flat against the posterior of his chest to position the tumor between them. The patient was given general anesthesia and the applicators 30 were energized at an indicated power level of 200 watts for 20 minutes at 13.56 mHz. The voltage (R.M.S.) across applicators 30 at this level was 100 volts. No measures were taken to insure intimate contact with the skin and applicators 30. Consequently, a skin burn resulted.

Three days later a thoracotomy was done to biopsy the lesion. The entire tumor was incised and a large biopsy taken. This biopsy was reported as inflammatory reaction only, although the surgeon was sure he had incised the tumor. Subsequently, the patient's course has shown gradual improvement. His brachial neuralgia has cleared and his chest X-rays are improved. The treatment resulted in considerable necrosis of the chest wall. This has now healed completely.

EXAMPLE II

In this Example the patient was a 57 year old white male who had undergone total laryngectomy for carcinoma of the vocal cords approximately two years before treatment. Approximately four months before treatment, the patient developed a large mass the size of an orange (3 inches in diameter) over the manubrium of the sternum (breastplate bone). Biopsy showed it to be a sqamous cell carcinoma.

The tumor was irradiated (Cobalt) but there was no substantial improvement and no reduction in the size of the mass. He was deemed inoperable by thoracic surgery. The tumor mass was stoney hard; the skin overlying the mass was stretched and shiny; and the tumor has pushed the tracheotomy to the right. There was also invasion of the underlying bone. The patient was having respiratory difficulty because the tumor compressed the trachea and his situation was desperate.

This patient was given four treatments utilizing generally the apparatus shown in FIG. 1 with the four inch applicators 30 described above in Example I. Prior to positioning the applicators, the skin of the patient was moistened with EKG jelly to decrease skin resistance, and a bronze wool sponge was placed over the location of the tumor on each side to maintain even electrical contact. One applicator 30 was then placed flat against the bronze sponge over the tumor with the second applicator 30 placed flat against the midaxilla. Thus, in effect, the patient's body was positioned between the two applicators 30 such that the tumor was located between them.

Indicated power was initially raised gradually to 300 watts (about 120 volts R.M.S. at 14.56 mHz) and maintained for 20 minutes between 275 and 300 watts.

One week later, the hard mass has become softer and fluctuant in parts. Ten days after the treatment the mass was aspirated and semi-liquid, necrotic material was withdrawn. In order to further liquify the necrotic material Bovine fibrinolysin and desoxyribonuclease were injected into the tumor. Two days later, the tumor was again aspirated.

Nineteen days after the first treatment, the patient was given a second treatment with the four inch applicators 30 again placed in the same manner except that the second applicator was placed on the back of the chest to the right of the midline. Treatment was for 20 minutes. Again the indicated power was gradually increased this time to 385 watts (135 volts R.M.S. at 13.56 mHz) and then varied between 350 and 410 watts during the remainder of the therapy.

Two weeks later, the tumor was aspirated again. Liquid material was obtained and the tumor was decreased considerably in size. No viable tumor cells were shown. There were some autolyzed cells. The third treatment immediately followed such aspiration and was similar to the first treatment except that initial power was 135 watts which was increased to 235 watts (108 volts R.M.S. at 13.56 mHz) and continued for a total of 11 minutes.

Although further therapy was considered superfluous, since the tumor had already been destroyed, a fourth treatment was given ten days later. In this instance, applicators 30 were placed one on the midaxilla, as described above, and the other first to the right and then to the left of the tumor. In each case, the skin was moistened with EKG jelly and bronze wool sponge is placed against the skin beneath the applicator 30 to maintain even electrical contact. The treatment was at 475 watts (150 volts R.M.S. at 13.56 mHz) on the left side for 20 minutes and at 375 to 400 watts (138 volts R.M.S. at 13.56 mHz) on the right side for 20 minutes.

The final pathological diagnosis indicated no malignancy. The mass has almost completely disappeared although there is some inflammation and an ulcer under the site of the necrotic tumor.

Before treatment in accordance with this invention the patient was having severe respiratory difficulty because the tumor was closing off his trachea just below the site of the tracheotomy. Since the treatment, the patient can breathe freely and has had no respiratory difficulty. Therapy in accordance with this invention resulted in minimal necrosis of the stretched skin over the lesion which will require future grafting.

EXAMPLE III

In this case the patient had what was considered to be a large, inoperable carcinoma of the lung which filled the entire right upper chest. The tumor mass was larger than the 4 inch applicators 30 which were available. One applicator 30 was put on the anterior portion of the chest wall after moistening the skin with conductive paste, and the other applicator 30 was similarly positioned on the posterior of the chest wall, such that the tumor mass was largely positioned between them. Fluoroscopy was utilized to define the location of the tumor mass. The patient was not anesthesized.

The apparatus was turned on to apply an indicated 50 watts and then increased to 256 watts (112 volts R.M.S. at 13.56 mHz) over a three minute interval. Power was then gradually decreased to 175 watts (90 volts) for the remainder of the period of 20 minutes.

Four days later the second treatment was given to the patient with the same positioning of applicators 30 in which power was gradually increased over a 9 minute period to 215 watts (105 volts) and then slowly lowered to 185 watts for 1 minute. The power level was then increased to 375 watts and kept for a four minute interval and thereafter between 300 and 350 watts for the rest of the 20 minutes. Because of the size of the applicators, the treatment was considered spacially inadequate to reach the entire tumor.

Five days later a right upper lobectomy was done. The entire right upper lobe was necrotic with severe inflammatory reaction. The entire lobe was fixed and cut on a large microtone. Ninety-nine percent of the tumor was necrosed but a small rim of tumor was still present where the applicators had not completely covered the tumor. All of the treated area was entirely free of tumor, as the tumor in the treated area was dead and undergoing autolysis.

In this case the inoperable carcinoma was considered to have been made operable since the tumor tissue adherent to the pleura and chest wall was completely necrotic and the lesion could be removed without leaving live tumor.

In each of the preceding Examples, the apparatus did not have provision for adjustable impedance matching or for measurement of forward and reflected power. The power levels indicated were based on input to the final stage of the amplifier and were probably two or three times that actually applied to the body being treated.

MEASUREMENTS OF TUMOR TEMPERATURE

Temperature recordings were made in human tumor tissue before and during R.F. therapy in six patients. Oral temperature was also recorded. In three patients, the temperature of the tissue adjacent to the located tumor tissue was also recorded. Temperature measurements were performed in those patients whose tumors were accessible to a needle type temperature probe. The $t°$ recorded in the tumor before and during R.F. treatment and body temperature is shown in Table I. The mean tumor temperature following R.F. treatment was significantly higher than that before treatment ($p < 0.001$) and that of body temperature ($p < 0.001$).

Table I:

| Patient | Temperature Elevation With R.F. (C°) | | | |
|---|---|---|---|---|
| | A. Max. Body T° during R. F. | B. Tumor Prior R. F. | C. T° during R. F. Treatment | D. Normal Adjacent Tissue T° |
| 1 | 37.5 | 39.1 | 48.0 | — |
| 2 | 38.5 | 37.2 | 48.5 | 40.0 |
| 3 | 38.0 | 38.0 | 49.5 | — |
| 4 | 38.2 | 38.0 | 48.5 | 39.7 |
| 5 | 36.0 | 37.2 | 46.0 | — |
| 6 | 37.0 | 37.6 | 49.0 | — |
| 7 | 37.1 | 37.2 | 49.5 | 39.0 |
| Mean | 37.5 | 37.9 | 48.4 | 39.5 |

Statistical analysis. Standard $p$ test for paired data. C vs. A, t=23.58 $p<0.001$; C vs. B, t=19.80 $p<0.001$.

Administration of Hypotensive Agents

As indicated above, inducing hypotension during treatment is useful in accentuating the differential heating of tumor tissue exposed to radio frequency electromagnetic radiation in accordance with this invention. The use of vasodilators, vasodepressors, anti-hypertensive agents and alpha blocking agents reduces the blood flow through the tumor. Typical agents which can be used are trimethaphan camsylate, erithrityl tetranitrate, amyl nitrate, and phentolamine. In inducing hypotension during radio frequency treatment in accordance with the present invention, the following procedure is suggested:

Hypotension is maintained at a level of about 60-70 mm. of mercury for the duration of a non-half hour radio frequency treatment. The tolerance of patients varies from individual to individual and some individuals can easily tolerate hypotension of 50 mm. of mercury for thirty minutes. Care is exercised to keep the head low especially if the part to be treated is elsewhere than the head. When trimethaphan camsylate (Arfonad) is the hypotensive agent, one ampule of 10 ml. of Arfonad containing 50 mg. per ml. is diluted to 500 cc. in 5% glucose in distilled water. An intravenous drip is started and the initial rate of administration given is 60 drops per minute. The blood pressure is taken every five minutes during the administration of the hypotensive agent. There is a marked variation in the patient's response and the rate of infusion must be frequently adjusted to maintain the blood pressure at the desired level. If there is any evidence of fainting or cerebral anoxia, the infusion is slowed and the blood pressure is allowed to come up to a higher level. In thin patients, the rate of drug administration can be as slow as four drops per minute, while in other patients, 100 drops per minute is sometimes required. Therefore, the blood pressure is used as an indication of proper dosage rather than the total amount of drug which the patient receives. The blood pressure promptly returns to normal upon cessation of the drug although the return toward normal can be hastened by the administration of vasopressor drugs.

I claim:

1. A method of treating a naturally occurring tumor in a human which comprises placing the portion of the body of the human in which the tumor is located in a radio frequency electromagnetic field thereby to heat the tumor tissue in said portion of said body by absorption of energy from said radio frequency electromagnetic field for a period of time and with intensity sufficient to cause necrosis of said tumor, but insufficient to cause significant damage to the adjacent normal tissue in said field.

2. The method of claim 1 in which the body portion is placed in a radio frequency field by positioning insulated, conductive metal plates in intimate contact with the portion of the body containing the tumor such that the tumor lies between the conductive metal plates, and applying radio frequency electrical power across said plates.

3. The method according to claim 2 in which the power level of radio frequency electrical power applied across said conductive metal plates is between 50 and 250 watts, in which the time of application is between 10 and 20 minutes and in which said plates are from 2 to 4 inches in diameter.

4. The method according to claim 1 in which the temperature of said tumor is raised above 46° C and in which the temperature of the normal tissue adjacent the tumor is kept below 40° C.

* * * * *